United States Patent
Poliac et al.

(10) Patent No.: US 7,166,076 B2
(45) Date of Patent: Jan. 23, 2007

(54) VASCULAR TESTING SYSTEM

(75) Inventors: Marius Poliac, Reno, NV (US); Gary Warner Blanch, Burnsville, MN (US); Victor Florin Glava, Little Canada, MN (US); Daniel James Ince, Lakeville, MN (US); Andrew Paul Karels, Savage, MN (US); William Lee Rogers, Oakdale, MN (US); John Alexander Romans, North Oaks, MN (US); Michael Jerome Siers, Duluth, MN (US); Charles Fredrec Steaderman, Burnsville, MN (US); Ricky Lee Grave, Kenosha, WI (US)

(73) Assignee: BioMedix, Inc., Vadnais Heights, MN (US)

(*) Notice: Subject to any disclaimer, the term of this patent is extended or adjusted under 35 U.S.C. 154(b) by 0 days.

(21) Appl. No.: 10/935,698

(22) Filed: Sep. 7, 2004

(65) Prior Publication Data

US 2006/0052713 A1    Mar. 9, 2006

(51) Int. Cl.
    *A61B 5/02* (2006.01)
(52) U.S. Cl. ............ 600/490; 600/494; 600/495
(58) Field of Classification Search ........ 600/481, 600/483, 484, 485, 488, 490–504
    See application file for complete search history.

(56) References Cited

U.S. PATENT DOCUMENTS

| | | | |
|---|---|---|---|
| 3,651,798 A | 3/1972 | Egli et al. | |
| 4,005,701 A | 2/1977 | Aisenberg et al. | |
| 4,800,892 A * | 1/1989 | Perry et al. | 600/490 |
| 4,830,019 A * | 5/1989 | Shirasaki et al. | 600/494 |
| 4,860,759 A | 8/1989 | Kahn et al. | |
| 5,337,751 A * | 8/1994 | Newell et al. | 600/495 |
| 5,368,039 A | 11/1994 | Moses | |
| 5,409,010 A * | 4/1995 | Beach et al. | 600/455 |
| 5,427,109 A | 6/1995 | Frankenreiter | |
| 5,477,162 A | 12/1995 | Heikkilä | |
| 5,579,776 A | 12/1996 | Medero | |
| 5,584,299 A | 12/1996 | Sakai et al. | |
| 5,606,977 A | 3/1997 | Ramsey, III et al. | |
| 5,626,151 A | 5/1997 | Linden | |
| 5,651,370 A | 7/1997 | Hersh et al. | |
| 5,810,734 A * | 9/1998 | Caro et al. | 600/485 |
| 5,868,679 A * | 2/1999 | Miyazaki | 600/494 |

(Continued)

FOREIGN PATENT DOCUMENTS

EP    0 765 630 A1    4/1997

*Primary Examiner*—Charles A Marmor, II
*Assistant Examiner*—Navin Natnithithadha
(74) *Attorney, Agent, or Firm*—Kinney & Lange, P.A.

(57) ABSTRACT

A vascular testing system includes a pressure applicator, a pressure source for generating fluid pressure at the pressure applicator; a variable orifice valve, and a valve control. The variable orifice valve is in fluid communication with the pressure applicator, and has an orifice size capable of dynamically changing. The valve control controls the variable orifice valve as a function of sensed pressure to produce substantially linear changes in pressure at the pressure applicator. Further, a method of vascular pressure measurement according to the present invention includes providing an applied pressure higher than a patient's systolic blood pressure at a vascular location, substantially linearly decreasing the applied pressure at the vascular location, and dynamically detecting vascular pressure oscillations at the vascular location as the applied pressure is decreased.

6 Claims, 10 Drawing Sheets

U.S. PATENT DOCUMENTS

| | | | |
|---|---|---|---|
| 6,093,152 A * | 7/2000 | Patterson | 600/495 |
| 6,228,036 B1 * | 5/2001 | Nakanishi | 600/491 |
| 6,485,429 B2 | 11/2002 | Forstner | |
| 6,520,919 B1 | 2/2003 | Nunome et al. | |
| 6,616,613 B1 | 9/2003 | Goodman | |
| 6,719,702 B2 * | 4/2004 | Lee et al. | 600/490 |
| 6,719,703 B2 * | 4/2004 | Chen et al. | 600/494 |
| 6,740,042 B1 | 5/2004 | Lerner et al. | |
| 6,808,496 B2 | 10/2004 | Oka et al. | |
| 2003/0212334 A1 | 11/2003 | Ogura et al. | |
| 2004/0249292 A1 | 12/2004 | Davis et al. | |

\* cited by examiner

VASCULAR TESTING SYSTEM

BACKGROUND OF THE INVENTION

Blood pressure measurement is generally referred to as sphygmomanometry. Segmental sphygmomanometry is measurement of blood pressures at different portions, or segments, of a patient's body. Often, bilateral vascular measurements are taken along symmetrical segments of a patient's body, for instance, left and right ankles, and left and right forearms. Segmental sphygmomanometry allows comparisons of blood pressures between segments and between symmetrically paired locations, which can provide information as to conditions of corresponding blood vessels. Peripheral arterial disease (PAD) is a condition where fatty deposits (or plaque) collect along walls of blood-carrying arteries. PAD is also known as atherosclerosis or the hardening of arteries. PAD is associated with a high risk of both fatal and nonfatal ischemic events, such as myocardial infarction (MI), stroke, and other thromboembolic events. However, once detected, plaque buildup associated with PAD can often be stopped or reduced.

One important and well-known blood pressure indicator is the ankle-brachial index (ABI). The ABI provides a ratio of a systolic blood pressure in a patient's ankle divided by a systolic blood pressure in the patient's arm. ABI readings that fall outside of a normal range (e.g., outside about 0.91 to about 1.30) and asymmetrical bilateral ABI readings (e.g., ABI readings that differ significantly between left and right limbs) are indicators that assist in diagnosis of PAD.

Segmental sphygmomanometry can be conducted at a vascular lab using non-invasive testing equipment. However, many patients do not undergo regular vascular testing. Moreover, PAD is generally under-diagnosed. Yet it is desirable to diagnose PAD prior to an ischemic event. More robust diagnoses of PAD are possible with the aid of segmental blood pressure testing in a primary care environment. Primary care is basic or general care usually given by doctors who work with general and family medicine, internal medicine (internists), pregnant women (obstetricians), and children (pediatricians). In addition, a nurse practitioner (NP), a State licensed registered nurse with special training, can also provide this basic level of health care. A substantial obstacle to providing segmental blood pressure testing in the primary care environment is the complexity of testing procedures and testing equipment.

Known segmental blood pressure testing equipment can include multiple pressure cuffs and multiple flow sensors, all of which require proper connection to testing control equipment and proper positioning relative to a patient's body. Generally, a segmental testing procedure is conducted as follows. A number of blood pressure cuffs are simultaneously placed on the extremities on which the pressure measurements are to be performed. Three locations are typically included: arm, ankle and toe. A flow sensor, such as a Doppler flow sensor, is placed over a desired artery distal to the inflated cuff. Then, in order to obtain a pressure measurement at a cuff, the cuff is inflated to a pressure higher than the patient's systolic blood pressure. The precise pressure level to which a cuff is inflated is determined by medical personnel (i.e., the primary care provider) operating the testing equipment. Inflation of a cuff temporarily halts blood flow at that cuff. Then the pressure in the cuff is gradually lowered by medical personnel, and a pressure reading is taken at the appearance of a distal blood flow (i.e., a return of blood flow), which is detectable with the flow sensor as a point of apparition of a pulsating waveform generated on a display screen of the testing equipment or as an audible nock.

Improper use of segmental blood pressure testing equipment due to inadequate training and incorrect technique can undermine diagnostic utility of the testing procedure. For instance, the flow sensor must be properly positioned relative to vasculature to obtain accurate results. Primary care providers can be overburdened by the use of complex segmental blood pressure testing equipment. Mover, documentation of vascular data is subjective, because operators select return of flow pressures based upon the appearance of an audible nock or by waveform interpretation. This presents an obstacle to obtaining accurate vascular test data in the primary care environment. Complexity and variability of prior art systems prevents primary care providers from integrating diagnostic procedure and practice, thereby inhibiting disease detection.

Diagnoses of cardiovascular conditions may require interpretation of vascular test data by a specialist. Vascular testing conducted in a primary care environment may require interpretation by a physician qualified in an appropriate specialty who is in a location physically remote from the primary care environment. Intercommunication of test data and test interpretation becomes important in providing quick diagnoses.

It is therefore desired to provide a vascular sensing system that is sufficiently easy to use in a primary care environment, so that primary care providers, such as technologists and primary care physicians, can reliably and accurately perform testing and acquire cardiovascular data. It is further desired to provide vascular test data to a qualified interpreting physician, who may be at a location remote from the primary care environment, thereby facilitating a diagnosis by a physician qualified in an appropriate specialty.

Thus, a reliable and accurate vascular testing system is needed that easily permits non-invasive measurement of vascular pressure characteristics in a primary care environment for assisting diagnosis of vascular conditions.

BRIEF SUMMARY OF THE INVENTION

The present invention relates to a testing system and method for measuring vascular pressures. The vascular testing system includes a pressure applicator, a pressure source for generating fluid pressure at the pressure applicator, a variable orifice valve, and a valve control. The variable orifice valve is in fluid communication with the pressure applicator, and has an orifice size capable of dynamically changing. The valve control controls the variable orifice valve as a function of sensed pressure to produce substantially linear changes in pressure at the pressure applicator.

Further, the method of vascular pressure measurement includes providing an applied pressure higher than a patient's systolic blood pressure at a vascular location, substantially linearly decreasing the applied pressure at the vascular location, and dynamically detecting vascular pressure oscillations at the vascular location as the applied pressure is decreased.

DETAILED DESCRIPTION

The present invention relates to a vascular testing system. More particularly, the present invention relates to a vascular testing system for non-invasive measurement of vascular pressure and flow characteristics in a primary care environment.

Vascular conditions such as peripheral arterial disease (PAD) are problematic. In general, and particularly where a patient exhibits one or more symptoms of PAD, it is desirable to conduct vascular testing in a primary care environment. PAD symptoms are present when patients experience leg pain with exercise, experience leg pain at rest, have a non-healing wound on a foot or leg, or have numbness or discoloration in a foot or leg. In addition, patients over the age of 70 having decreased pedal pulses and patients over the age of 50 who smoke and/or have diabetes and have decreased pedal pulses are at risk for PAD.

Segmental sphygmomanometry is measurement of blood pressures at different portions, or segments, of a patient's body. Bilateral vascular measurements are measurements taken along symmetrical segments of a patient's body, for instance, left and right ankles, and left and right forearms. Segmental sphygmomanometry allows comparisons of blood pressures between segments and between symmetrically paired locations, which can provide information as to conditions of corresponding blood vessels. One important and well-known segmental blood pressure indicator is the ankle-brachial index (ABI).

Another vascular test is pulse volume recording (PVR). PVR involves the use of pressure cuffs to determine characteristics of blood flow by measuring a volume change in a limb segment. This is achieved by inflating a pressure cuff so that it is sensitive to the swelling and contraction of a limb segment with each heartbeat, but not tight enough to prevent blood flow. In that way blood volume changes per cardiac cycle can be measured.

Figure 1:
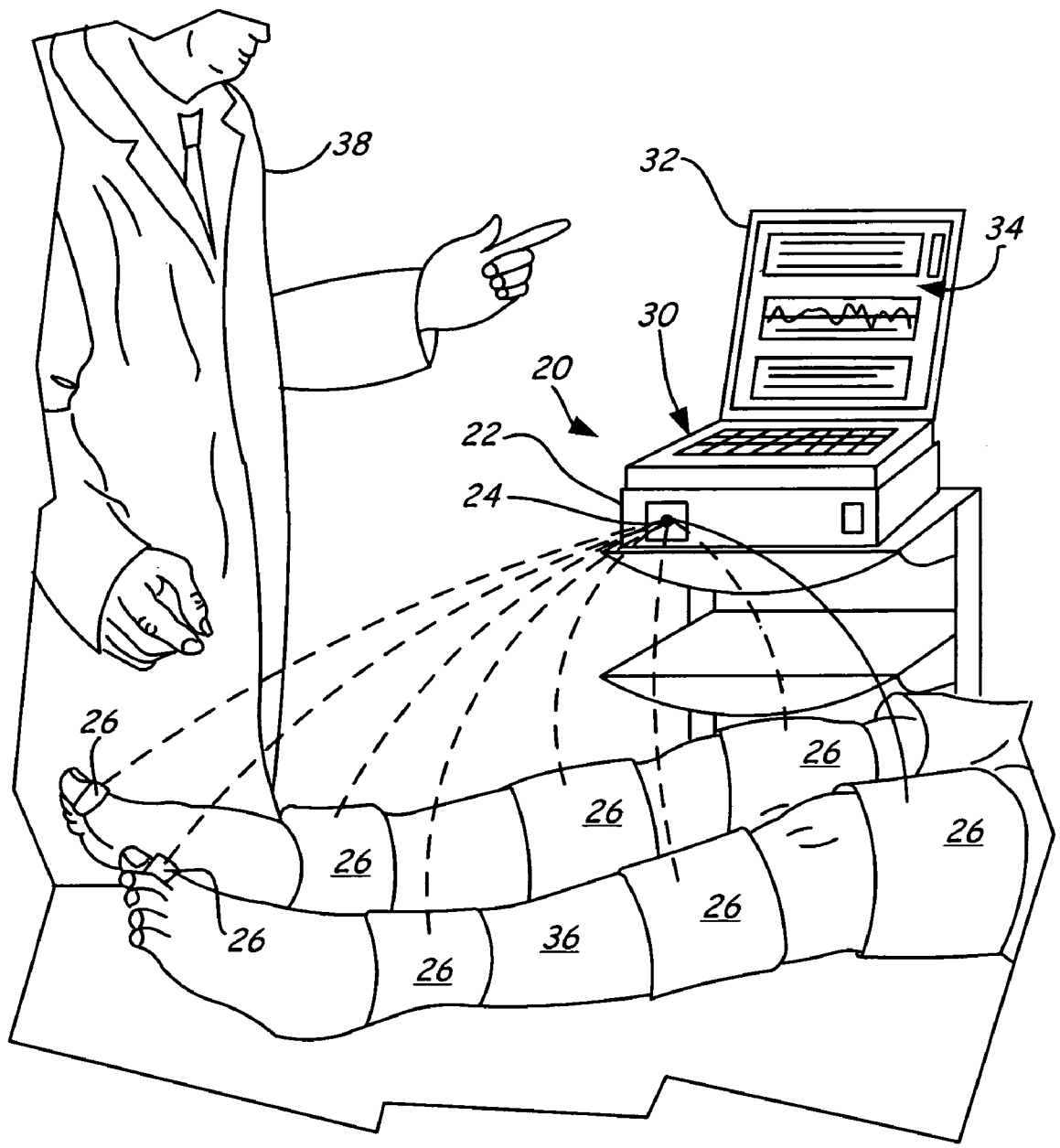
FIG. 1 is an exemplary representation of an arrangement of a vascular sensing system.

FIG. 1 is an exemplary representation of an arrangement of a vascular testing system 20. The vascular testing system 20 includes a diagnostic test unit 22 having a single air outlet 24, and one or more pressure applicators 26. The diagnostic test unit 22 can be connected to a computer 30 having a display 32 for providing an interface 34 with the vascular testing system 20.

As shown in FIG. 1, the vascular testing system 20 is utilized in a primary care environment for sensing and testing vascular conditions of a patient 36. A care provider 38, such as a lab technician or a primary care physician, can position the one or more pressure applicators 26 along the patient's 36 body. The one or more pressure applicators 26 are oscillometric pressure cuffs. Each of the pressure applicators 26 can be positioned at an exterior location along the patient's 36 body for sensing vascular pressures at desired vascular locations, such as at toes, ankles, thighs and arms. One or more pressure applicators 26 can be placed on a patient's 36 body at a time.

In the embodiment shown in FIG. 1, the diagnostic test unit 22 includes a single air outlet 24 such that only one pressure applicator 26 can be connected to the diagnostic test unit 22 at a time. The interface 34 permits display of instructions for guiding the care provider 38 through a process of engagement and disengagement of particular pressure applicators 26 positioned at particular vascular locations, (such as those shown in FIG. 2) to the air outlet 24 of the diagnostic test unit 22.

Each of the pressure applicators 26 can be attached to the air outlet 24 of the diagnostic test unit 22, in fluid communication therebetween. Tubing or other suitable connectors can be used to connect each of the pressure applicators 26 to the diagnostic test unit 22. Because the diagnostic test unit 22 has a single air outlet 24 in the embodiment shown in FIG. 1, only a single pressure applicator 26 is connected to the diagnostic test unit 22 at one time. This minimizes a risk of improper connections, and generally simplifies set-up of the vascular testing system 20.

The diagnostic test unit 22 is capable of continuously streaming raw pressure data to the interface 34 during operation. The diagnostic test unit 22 can be connected to the computer 30, which can be a PC type desktop or laptop computer. The computer 30 permits, inter alia, collecting, sorting, interpretering, organizing, displaying and transmitting data from the diagnostic test unit 22. The computer 30 operatively communicates with the interface 34.

Generally, the interface 34 permits interaction with the vascular testing system 20 by the care provider 38. The interface 34 in the primary care environment allows display of measurements sensed by the vascular testing system 20, such as current pressure reading values and captured waveform data. The interface 34 further allows the care provider 38 to enter patient data to a database, which facilitates coordination of various patient data with information collected as part of vascular testing. The interface 34 can include forms and displays for patient information, insurance information, history/risk factors, visit data, indications of a test, results of a test, interpretation (this function can be disabled until the test is signed by a qualified diagnosing physician), and reporting. In addition, the interface 34 can provide suitable appointment, scheduling and billing functionality. In one embodiment, the interface 34 includes software compatible with Microsoft WINDOWS operating systems. In further embodiments, the interface 34 may include other types of software (e.g., software compatible with UNIX, LINUX, MACINTOSH, or other operating systems).

The vascular testing system 20 can be connected to the Internet, via a modem or other similar device, for communicating with servers and a remote interface. For instance, data collected in the primary care environment can be transmitted over the Internet or other network, via file transfer protocol (FTP) or other suitable means, to a database server (not shown) that in turn communicates with an interface (not shown) physically remote from the primary care environment, such as at a specialized vascular laboratory. Data can thereby be transmitted, with appropriate compression and/or encryption, between an interface on a technician-side (e.g., the interface 34 in the primary care environment) and a specialist-side interface (e.g., an interface in a vascular laboratory). Transmittal of vascular data collected in the primary care environment can be transmitted to a qualified interpreting physician, such as a specialist in an appropriate vascular field, for interpreting the data and making a diagnosis.

An Internet-compatible vascular testing system can be configured such as that described in U.S. patent application Ser. No. 10/227,770, entitled SYSTEM AND METHOD FOR TESTING FOR CARDIOVASCULAR DISEASE, which is hereby incorporated by reference in its entirety.

Figure 2:
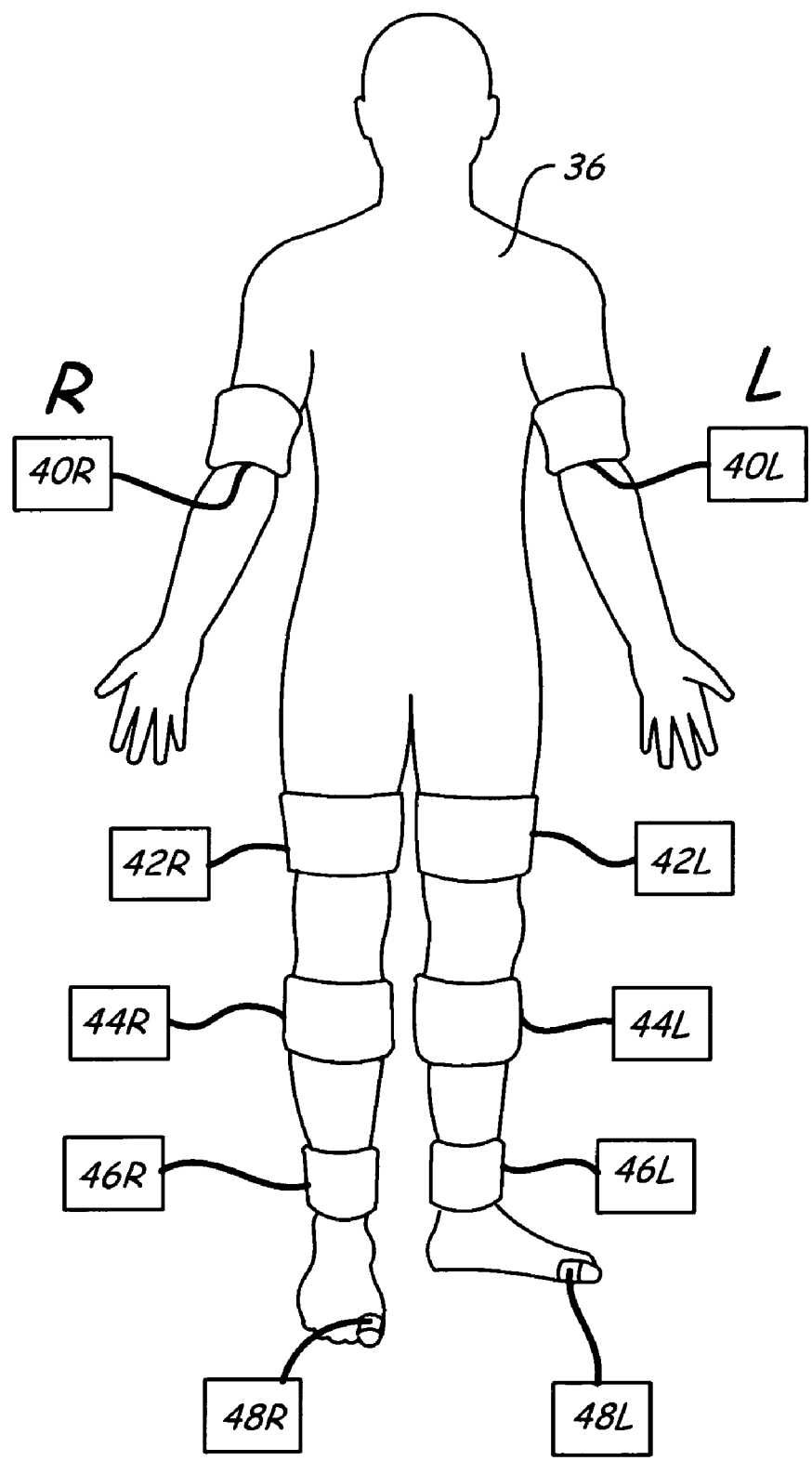
FIG. 2 is an exemplary representation of vascular testing locations.

FIG. 2 is an explementary representation of vascular testing locations, including arm locations 40L and 40R, thigh locations 42L and 42R, calf locations 44L and 44R, ankle locations 46L and 46R, and toe locations 48L and 48R.

Segmental pressure testing can be conducted at vascular locations such as the arm locations 40L and 40R, the ankle locations 46L and 46R, and the toe locations 48L and 48R. PVR testing can be conducted at vascular locations such as the thigh locations 42L and 42R, the calf locations 44L and 44R, and the ankle locations 46L and 46R. Pressure measurements at particular vascular locations are generally taken over a period of about 15 seconds to about 60 seconds.

Figure 3:
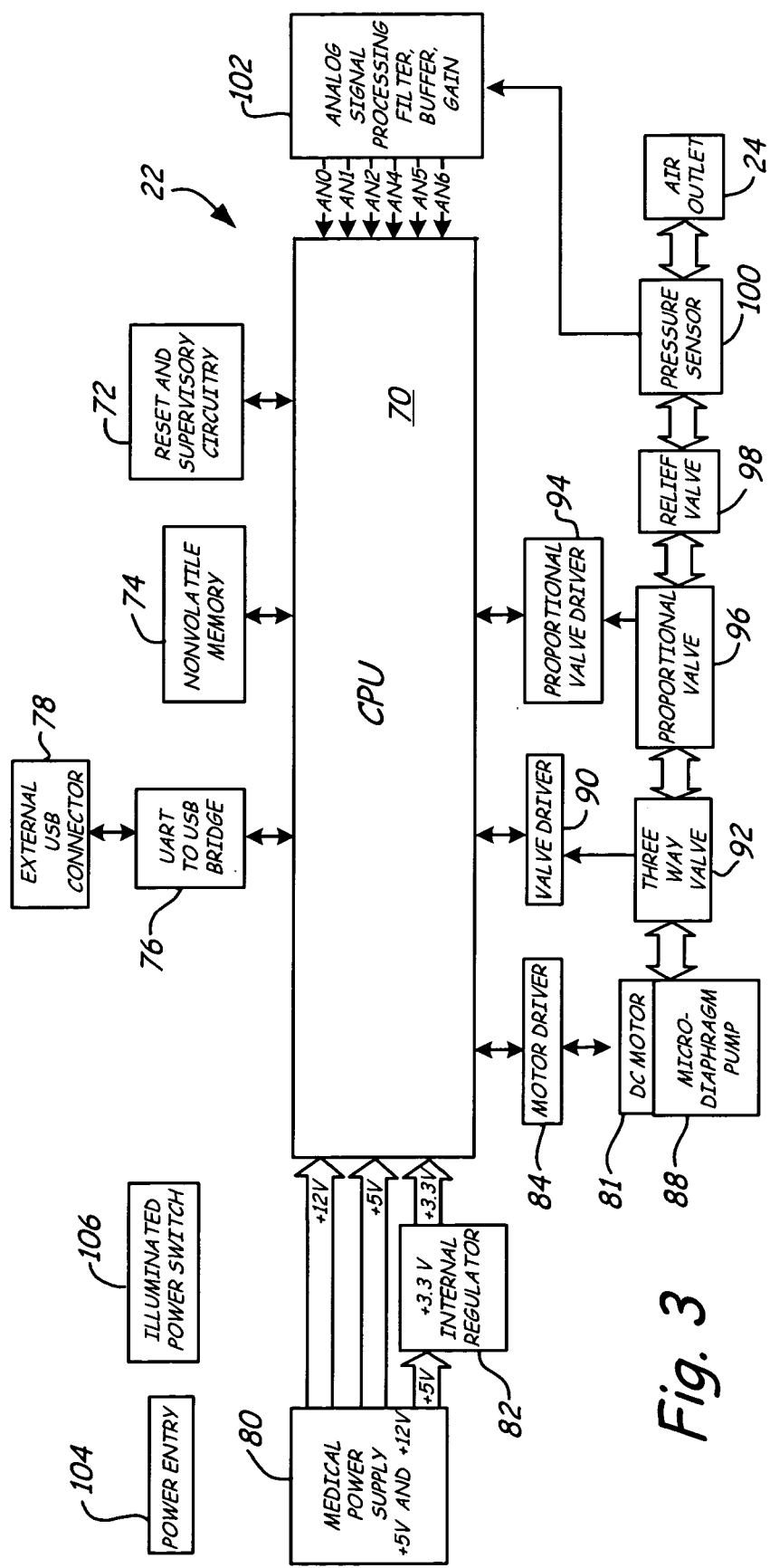
FIG. 3 is a block diagram of a diagnostic test unit.

FIG. 3 is a block diagram of the diagnostic test unit 22. The diagnostic test unit 22 includes a central processing unit (CPU) 70, reset and supervisory circuitry 72, non-volatile memory 74, a bridge 76, an external connector 78, a medical power supply 80, an internal power regulator 82, and means for controlling pressure in a pressure applicator including a motor driver 84, an electric motor 86 (e.g., a DC motor), a micro-diaphragm pump 88, a first valve 90, a first valve 92, a proportional valve driver 94, a variable orifice valve 96 (e.g., a proportional valve), a relief valve 98, a pressure sensor 100, and an air outlet 24. The diagnostic test unit also includes a signal processor 102. The diagnostic test unit 22 can further include a power entry 104 and an power switch 106.

The reset and supervisory circuitry 72 and non-volatile memory 74 are operatively connected to the CPU 70. The external connector 78, which can be a universal serial bus (USB) connector, is operatively connected to the CPU 70 via the bridge 76. The medical power supply 80 provides two distinct supply voltages to the diagnostic test unit 22 (e.g., providing voltages of 12 volts and 5 volts). The medical power supply 80 further supplies power to the internal regulator 82, which in turn can supply power at a third voltage (e.g., 3.3 volts).

The electric motor 86 is operatably connected to the mirco-diaphragm pump 88 and to the CPU 70 via the motor driver 84. The micro-diaphragm pump 88 is in fluid communication with the first valve 92, which is operatably connected to the CPU 70 via the first valve driver 90. The variable orifice valve 96 is in fluid communication with the first valve 92, and is operatably connected to the CPU 70 via the variable orifice valve driver 94. The relief valve 98 is in fluid communication with the variable orifice valve 96. The pressure sensor 100 is in fluid communication with the relief valve 98 and the air outlet 24. The pressure sensor 100 is disposed between the valves 92, 96, 98 and the air outlet 24, and does not contact a patient's body. Further, output from the pressure sensor 100 can be transmitted to the signal processor 102, which is electrically connected to the CPU 70.

The CPU 70 provides control of functions of the diagnostic test unit 22, such as actuating the electric motor 86 and controlling valves (e.g., the variable orifice valve 96). In one embodiment, the CPU 70 is a model HD64F2317 16 Bit CPU available from Hitachi America, Ltd., Brisbane, Calif.

The external connector 78 permits the diagnostic test unit 22 to be connected to other devices, such as the computer 30 shown in FIG. 1.

The electric motor 86 drives the micro-diaphragm pump 88 to generate a fluid displacement pressure. Typically, a fluid displaced by the micro-diaphragm pump 88 is air. The micro-diaphragm pump 88 is connected in fluid communication with a series of one or more valves 92, 96, 98 by suitable tubing or the like. A one-way check valve (not shown) can be included with the micro-diaphragm pump 88 for preventing fluid flow back through the pump 88.

The first valve 92 is generally positioned adjacent the micro-diaphragm pump 88. In one embodiment, the first valve 92 is an on/off valve capable of connecting a fluid path to the pressure applicator 26 to either the pump (i.e., an "on" position) or to atmosphere (i.e., an "off" position). The variable orifice valve 96 is positioned adjacent the first valve 92 and distal to the micro-diaphragm pump 88. The variable orifice valve 96 has a variable orifice size capable of dynamically changing. In one embodiment, the variable orifice valve 96 is a special proportional valve model EV-P-10-2507, available from Clippard Instrument Laboratory, Inc., Cincinnati, Ohio.

The relief valve 98 is a mechanical valve positioned adjacent the variable orifice valve 96 and distal to the micro-diaphragm pump 88. The relief valve 98 facilitates safety monitoring by permitting the vascular testing system 20 to prevent pressure in a pressure applicator from exceeding a maximum value. For example, pressure in a pressure applicator can be prevented from exceeding about 240 millimeters mercury (mmHg) (e.g., using a 4.6 PSI relief valve).

The pressure sensor 100 permits measurement of pressures at any pressure applicator connected to the air outlet 24, thereby allowing measurement of vascular characteristics at a corresponding vascular location. Signals from the pressure sensor 100 are transmitted to the signal processor 102. The signal processor 102 can provide various standard forms of signal processing, such as analog-to-digital conversion, filtering, buffering, and gain adjustments. The signal processor 102 can be an analog signal processor. Signals are transmitted from the signal processor 102 to the CPU 70. Additional safety protocol can be used. The first valve 92 can be used to prevent pressures from remaining in the system more than a pre-determined period of time. For example, pressures at and above about 220 mmHg may be allowed only for a period of 5 seconds, and any significant system pressure (e.g., a system pressure at and above about 15 mmHg) may be allowed only for a period of 180 seconds. When pressures remain in the system beyond the desired time period, the first valve 92 can be used to release pressure (e.g., vent fluid to the atmosphere).

An exemplary method of obtaining vascular measurements according to the present invention is now described. In operation, one or more pressure applicators or pressure cuffs are positioned at vascular locations at which a vascular pressure measurement is to be performed. An operative pressure cuff is first inflated to a pressure higher than a patient's systolic blood pressure, which occludes a blood vessel (i.e., causes a portion of a blood vessel to collapse and stop blood flow) at the vascular location. The particular level of pressure to which the operative pressure cuff is inflated is determined by the care provider 38 operating the vascular testing system 20. After the blood vessel at the vascular location is occluded, pressure in the operative pressure cuff is automatically and gradually lessened. Pressure is gradually lessened in a slow, controlled manner (e.g., at a rate of about 3 to about 5 mmHg/second). Oscillations in pressure at the operative pressure cuff are caused by the patient's artery as the pressure in the pressure cuff is gradually decreased.

Pressure can be decreased in a number of ways, such as by decreasing the pressure supplied by the micro-diaphragm pump 88 or by adjusting the orifice size of the variable orifice valve 96. In one embodiment, the size of the variable orifice valve 96 is utilized to adjust the applied pressure. The orifice size of the variable orifice valve 96 changes in order to maintain a generally linear decrease in pressure applied to the operative pressure cuff. A fixed orifice valve would exhibit an exponential bleed rate, whereas a generally linear bleed rate is desired. Size of the orifice can be controlled with software operative through the CPU 70. Use of the variable orifice valve 96 to control applied pressure at an operative pressure applicator permits pressure readings to be obtained quickly.

Figure 4:
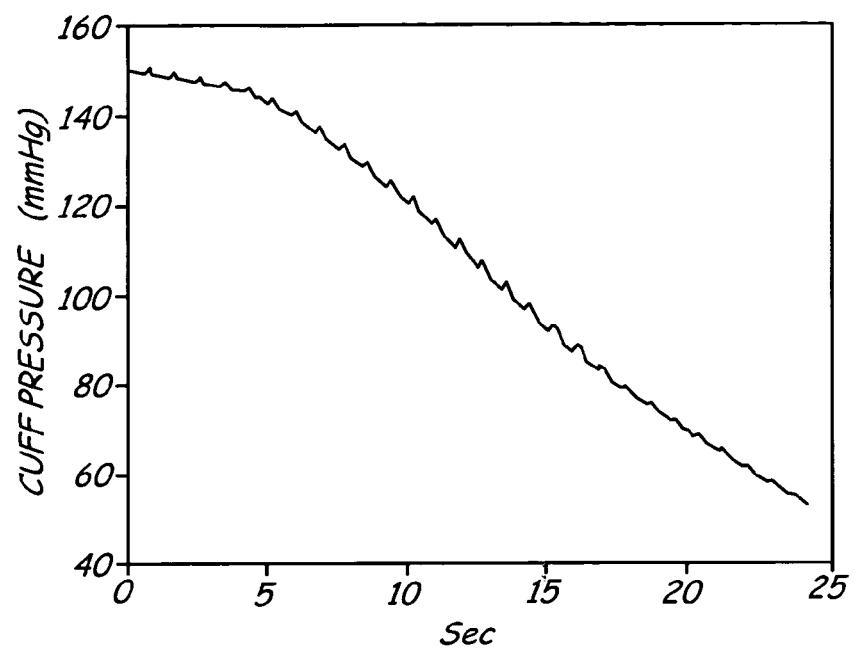
FIG. 4 is a graph of a cuff pressure signal over time, as cuff pressure is gradually decreased.

FIG. 4 is a graph of a cuff pressure signal over time, as cuff pressure is gradually decreased. It is desirable to decrease the cuff pressure in a generally linear manner. Oscillations in pressure at the operative pressure cuff are recorded and amplified by the vascular testing system 20. Such oscillations are indicative of blood flow conditions at the vascular location.

Figure 5:
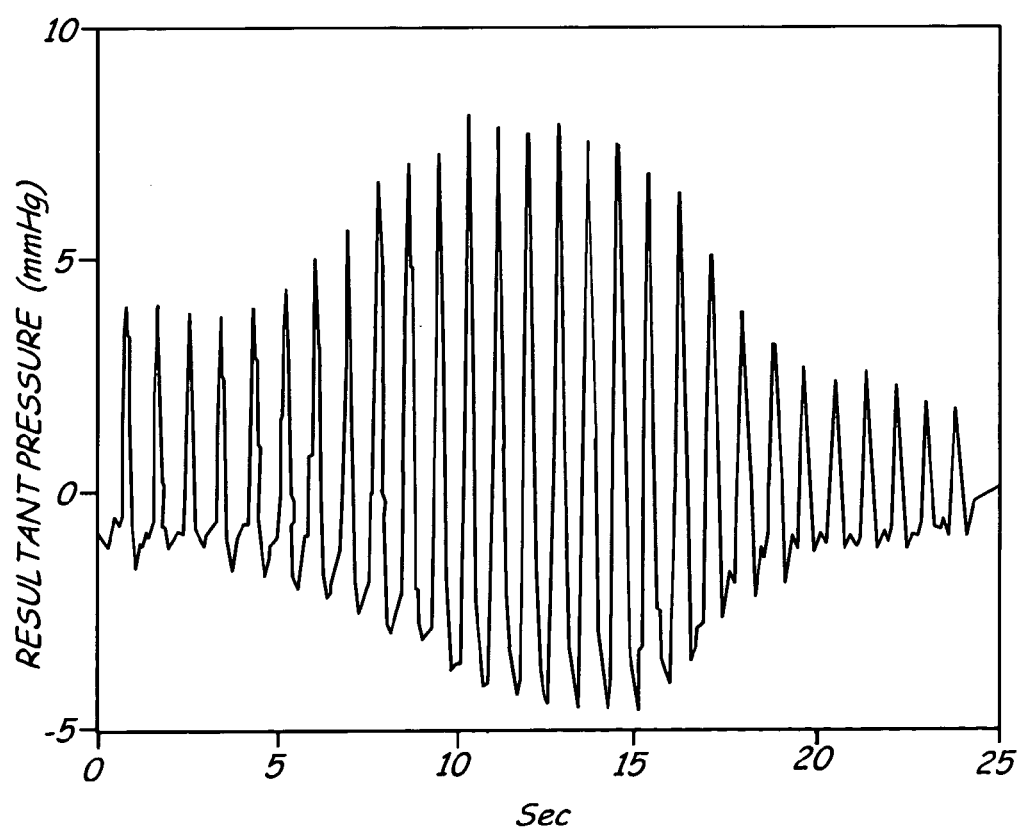
FIG. 5 is a graph of resultant pressure oscillations in the cuff pressure signal of FIG. 4.

The cuff pressure signal is adjusted to compensate for the decreasing pressure applied to the operative pressure cuff by the micro-diaphragm pump 88. Generally, this involves removing the ramp-shaped bias signal corresponding to the pressure applied to the operative pressure cuff. FIG. 5 is a graph of result in pressure oscillations in the cuff pressure signal of FIG. 4 after adjustment. Calculations, adjustments, and other appropriate data manipulation can generally be accomplished through software. Calculations, waveform analysis, and other data manipulation can be accomplished through the computer 30 and software of the interface 34. In further embodiments, software for performing calculations, etc., can be operative through the CPU 70 of the diagnostic test unit 22.

Figure 6:
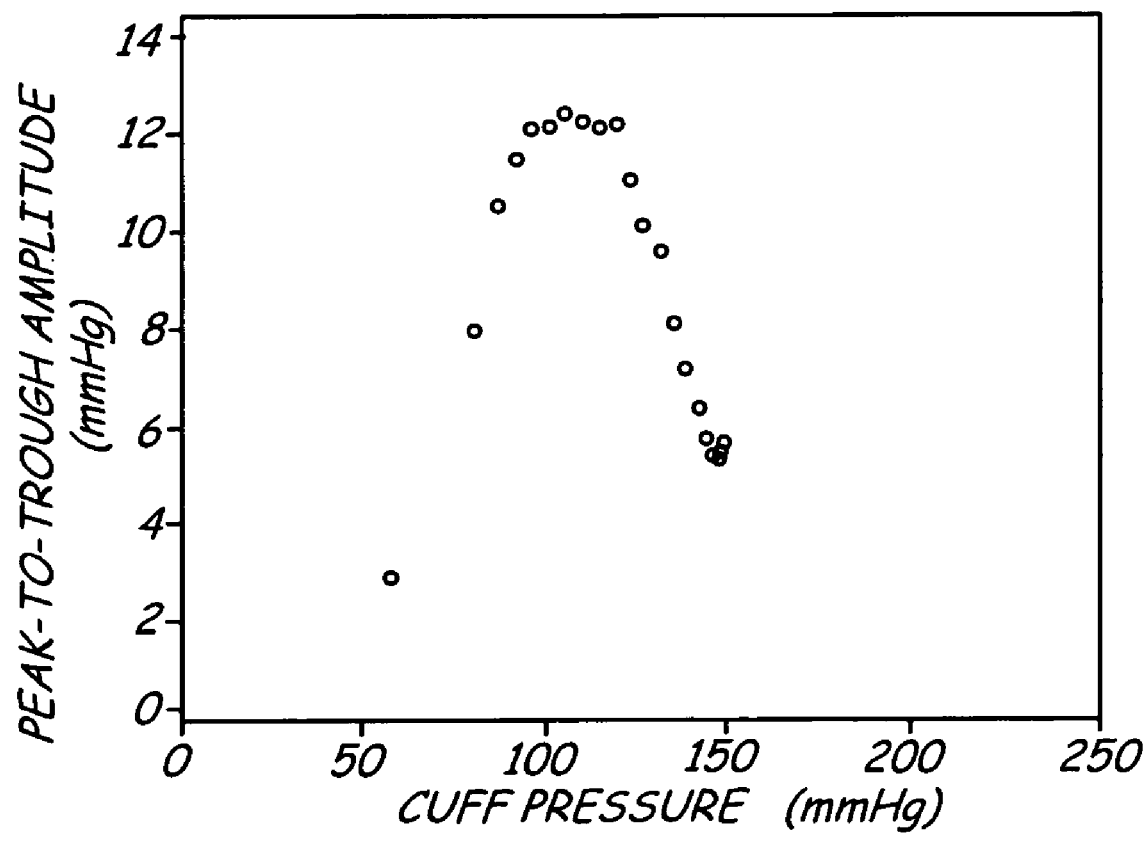
FIG. 6 is a graph plotting peak-to-trough pressure amplitude of the pressure oscillations of FIG. 5 versus the corresponding cuff pressure of FIG. 4.

FIG. 6 is a graph plotting peak-to-trough pressure amplitude of the pressure oscillations of FIG. 5 versus the corresponding cuff pressure of FIG. 4. FIG. 6 represents raw data points corresponding to the amplitudes of the pressure oscillations.

Figure 7:
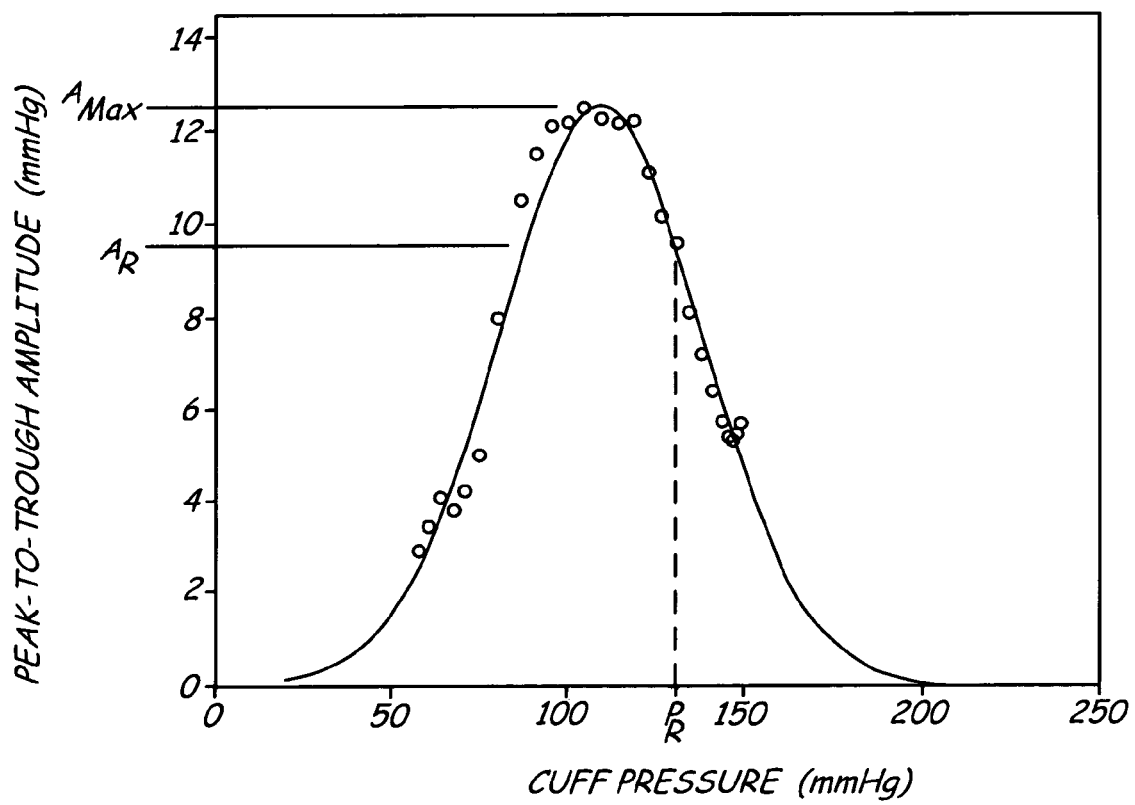
FIG. 7 is a graph of a bell-shaped curve fitted to the plot of FIG. 6.

After the amplitudes of pressure oscillations are collected, a bell-shaped curve is fitted to the raw data points obtained. Some noise filtering can occur throughout this process. FIG. 7 is a graph of a bell-shaped curve fitted to the plot of FIG. 6. A peak amplitude of the curve, $A_{Max}$, is determined. $A_{Max}$ is typically determined according the bell-shaped curve, rather than by the raw data points themselves. Next, a return of blood flow is determined as a ratio of $A_{Max}$. First, a value $A_R$ is identified at a pre-determined percentage (e.g., seventy-five percent [75%]) of $A_{Max}$. The value of $A_R$ is indicative of a pressure oscillation amplitude at which blood flow returns at the vascular location. Next, a cuff pressure $P_R$ corresponding to the peak-to-trough amplitude $A_R$, and taken along a higher pressure slope of the curve (i.e., the right-hand slope of the curve as shown in FIG. 7), is recorded as the patient's return of blood flow pressure. The pressure $P_R$ corresponds to a pressure measurement obtained by care providers using known types of vascular testing equipment (e.g., Doppler flow sensors).

Vascular testing at some vascular locations is facilitated by additional filtering and data processing. For instance, vascular locations on digits, such as on a toe, require the use of relatively small pressure cuffs sized to fit those locations. Vascular testing using relatively small pressure cuffs presents significant concerns with signal noise. In such situations, a signal-to-noise ratio is more problematic than for vascular measurements taken with relatively large pressure cuffs used on ankles, arms, etc. Methods of digit pressure filtering can be used to alleviate concerns with noise for vascular testing at vascular locations on digits.

Figure 8:
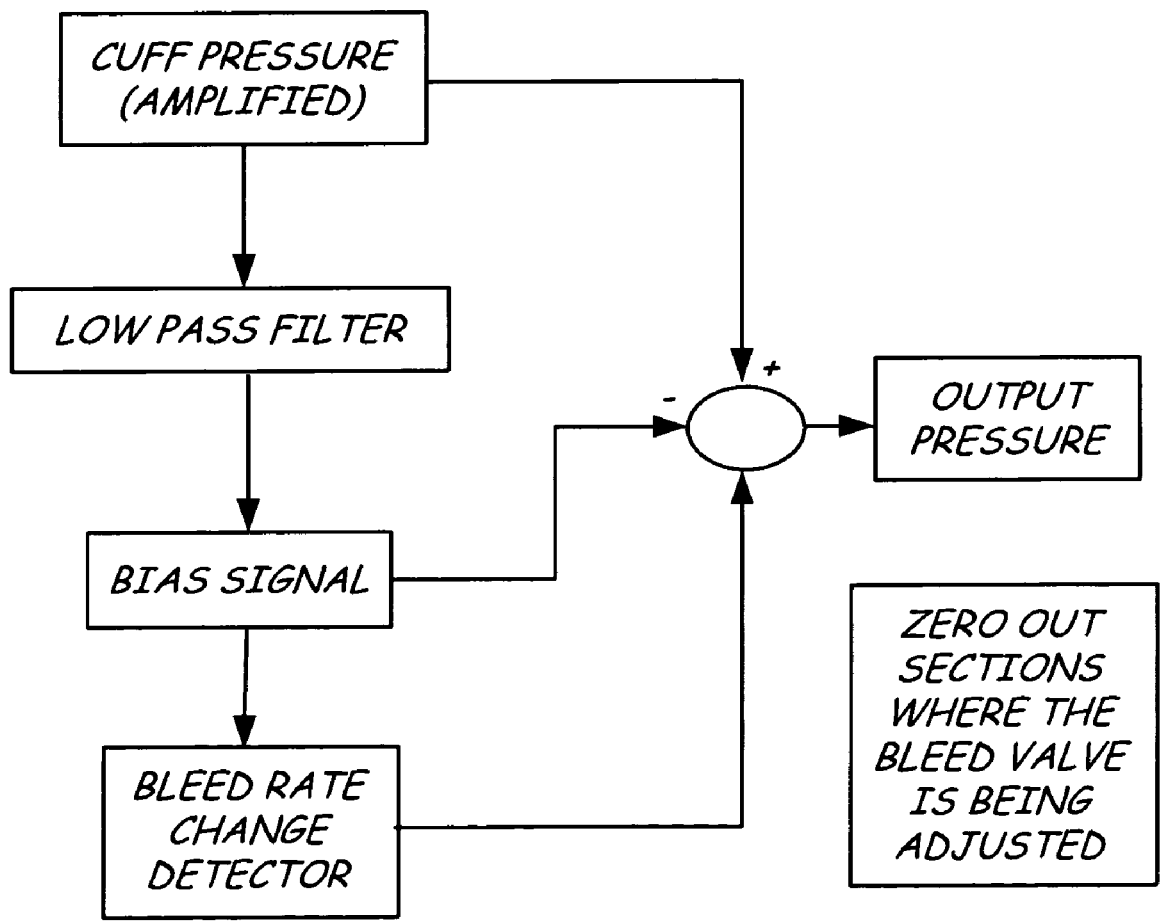
FIG. 8 is a block diagram of a digit pressure filtering algorithm.

FIG. 8 is a block diagapham of a digit pressure filtering algorithm. The digit pressure filtering algorithm is useful in taking pressure measurements at a vascular location on a digit (e.g., the toe locations 48L and 48R shown in FIG. 2).

As seen in FIG. 8, an amplified cuff pressure signal is obtained. The amplified cuff pressure signal is also passed through a low pass filter. A bias signal is determined after the amplified cuff pressure signal is filtered. A bleed rate change detector permits detection of a rate of change in applied pressure, as applied pressure is decreased. This permits the vascular testing system 20 to zero out sections of the bias signal where the bleed valve is being adjusted. Using the digit pressure filtering algorithm, the vascular testing system 20 can determine an output or resultant pressure.

Figure 9:
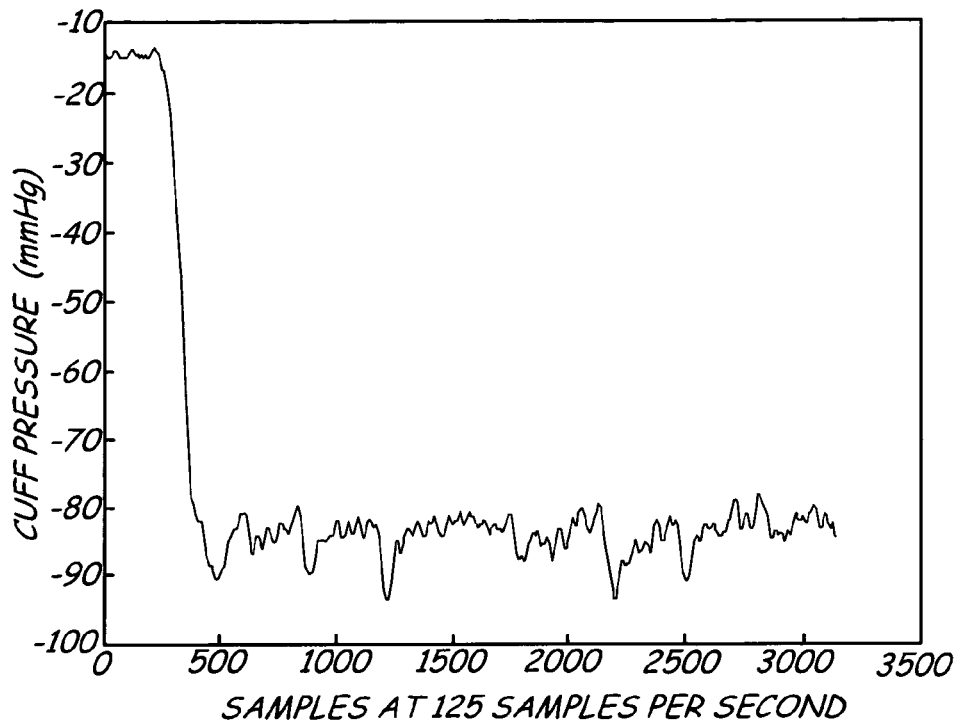
FIG. 9 is a graph of an amplified pressure signal.

FIG. 9 is a graph of an amplified pressure signal from a vascular location on a digit. This amplified pressure signal is similar to that shown and described with respect to FIG. 4.

Figure 10:
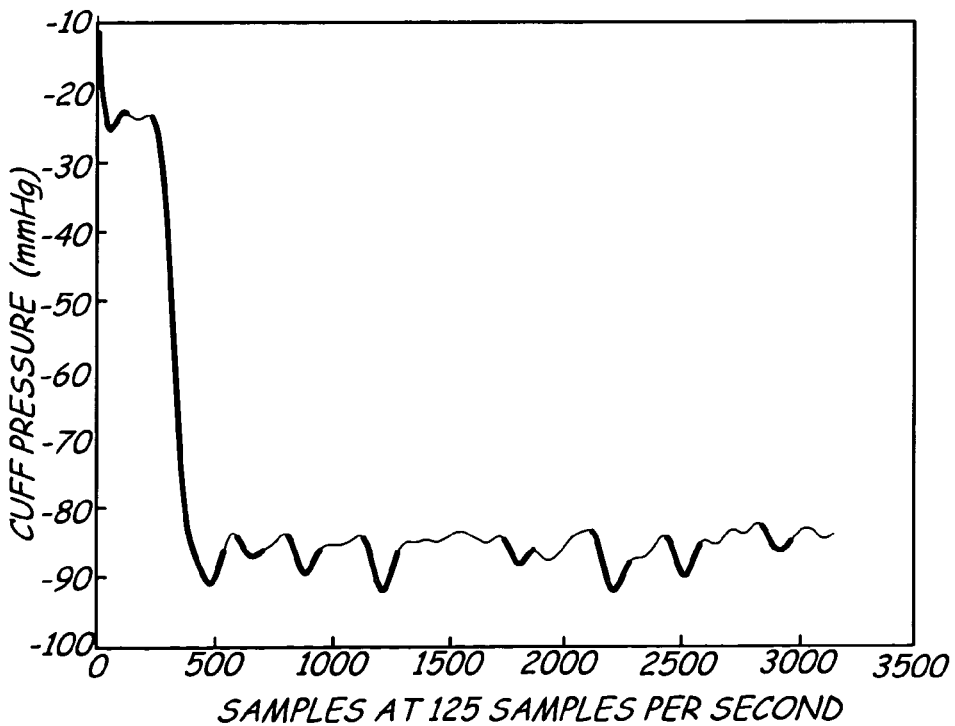
FIG. 10 is a graph of a bias signal corresponding to the pressure signal of FIG. 9.

FIG. 10 is a graph of a bias signal curve corresponding to the pressure signal of FIG. 9 after filtering. Portions of negative flow in the bias signal followed by a window of positive flow are shown in FIG. 10 with a heavy line weight. Those weighted portions of the bias signal curve correspond to intervals where the bleed valve is being adjusted, meaning that an orifice size of a variable orifice (e.g., proportional) valve is changing. The orifice size of the variable orifice valve 96 changes in order to maintain a generally linear decrease in pressure applied to the pressure applicator 26.

Figure 11:
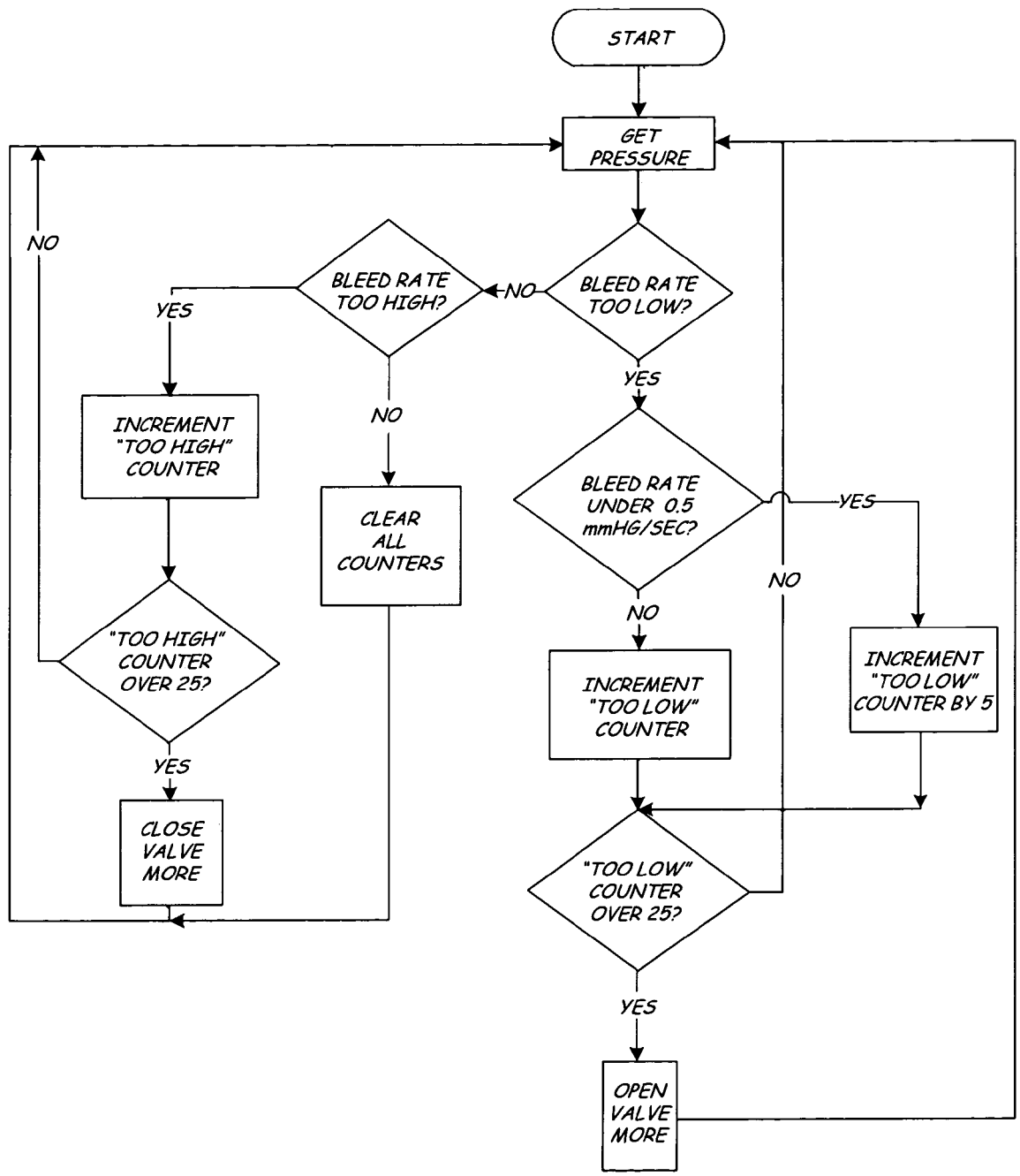
FIG. 11 is a flow chart of a bleed rate adjustment algorithm.

FIG. 11 is a flow chart of a bleed rate adjustment algorithm. The algorithm shown in FIG. 11 permits opening of the valve more where a bleed rate is too low, and closing the valve more when the bleed rate is too high. In one embodiment, counters are used to increment a counter value when the bleed rate is outside a desired range. When the counter reaches a predetermined value (e.g., 25), the variable orifice valve 96 is opened or closed more, as appropriate.

Figure 12:
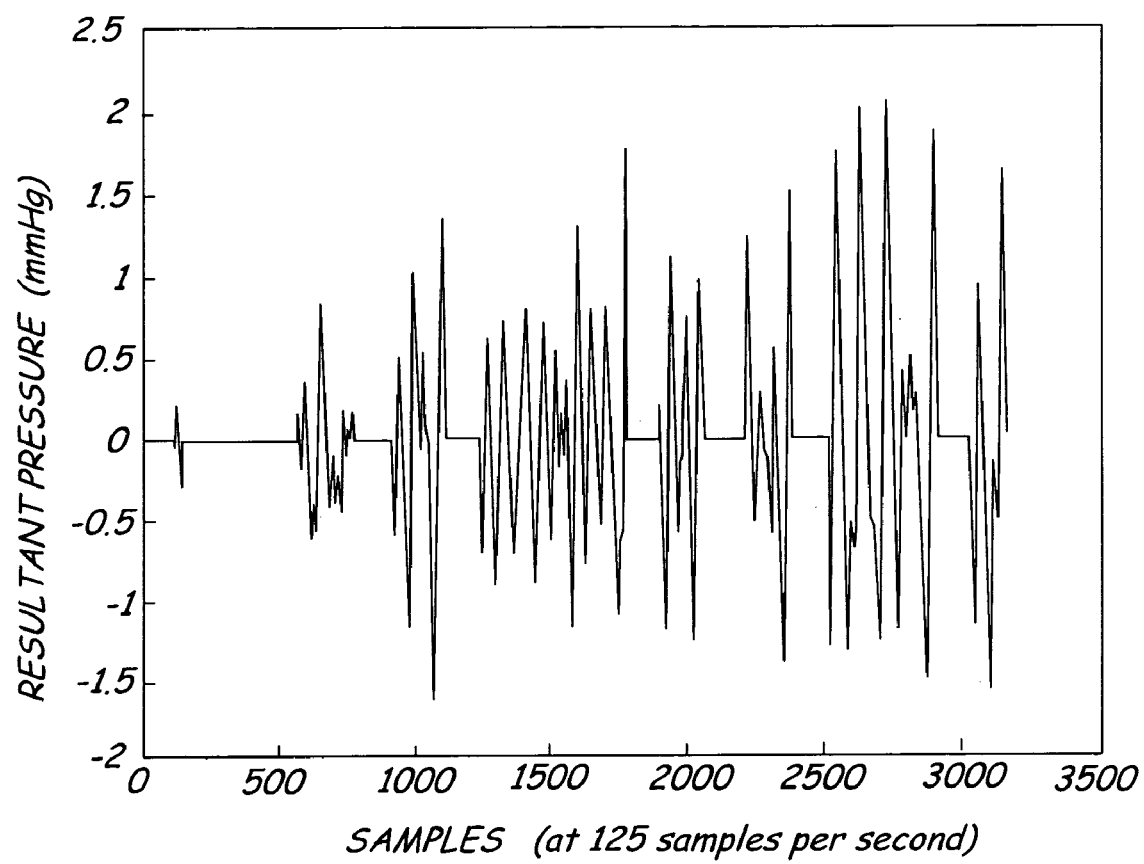
FIG. 12 is a graph of resultant cuff pressure oscillations after adjustment.

FIG. 12 is a graph of resultant cuff pressure oscillations after adjustment. Changing the size of the orifice introduces noise signals. Adjustment involves removing the bias signal from the amplified pressure signal and zeroing out intervals of bleed valve adjustment (i.e., regions of the bias signal curve indicated with a heavy line weight). The resultant pressure graph of FIG. 12 is similar to that shown in FIG. 5. A return of flow pressure at the vascular location (e.g., the toe locations 48L and 48R shown in FIG. 2) is then determined in a similar manner to that shown and described with respect to FIGS. 6 and 7. A pressure of return of blood flow, $P_R$, can be determined as a ratio of a peak pressure oscillation amplitude $A_{Max}$, such as at a point $A_R$ that is 75% of $A_{Max}$.

A pressure of return of blood flow, $P_R$, obtained using any of the equipment and processes shown and described above can be utilized in diagnoses of vascular conditions. Values of $P_R$ may differ from systolic pressures. Regardless, values of $P_R$ can be used in segmental comparisons like the ABI, in a manner similar to the systolic pressures traditionally used in the ABI.

In addition to the testing processes shown and described above, the vascular testing system 20 can further take sphygmomanometric measurements such as systolic, mean and diastolic blood pressures using conventional measurement techniques. Such conventional techniques will be readily apparent to those skilled in the art.

Although the present invention has been described with reference to preferred embodiments, workers skilled in the art will recognize that changes may be made in form and detail without departing from the spirit and scope of the invention. For instance, vascular testing locations can include locations on a patient's body other than those specifically enumerated above.

The invention claimed is:

1. A vascular testing system comprising:
    a pressure applicator;
    a pressure source for generating fluid pressure at the pressure applicator;
    a variable orifice valve in fluid communication with the pressure applicator, wherein the valve has an orifice size capable of dynamically changing;
    a pressure sensor operably connected between the pressure applicator and the variable orifice valve;
    a valve control for controlling the variable orifice valve as a function of pressure sensed by the pressure sensor to produce substantially linear changes in pressure at the pressure applicator; and
    a control device for causing the vascular testing system to determine a peak pressure oscillation amplitude as a function of pressure sensed by the pressure sensor as pressure applied by the pressure applicator is lessened, and to determine a first pressure value that corresponds to a pressure oscillation amplitude at approximately seventy-five percent (75%) of a peak pressure oscillation amplitude and at a pressure greater than a pressure value corresponding to the peak pressure oscillation amplitude, and to produce an output of the first pressure value identified as a pressure at a return of blood flow at a vascular location adjacent the pressure applicator.

2. The vascular testing system of claim 1, wherein the pressure applicator is an oscillometric pressure cuff.

3. The vascular testing system of claim 2, wherein the oscillometric pressure cuff is sized to fit on a human toe.

4. A method of vascular pressure measurement, the method comprising:
    providing an applied pressure at a vascular location, wherein the applied pressure is higher than a patient's systolic blood pressure;
    substantially linearly decreasing the applied pressure at the vascular location;
    dynamically detecting vascular pressure oscillations at the vascular location as the applied pressure is decreased;
    determining a first pressure value corresponding to an oscillation amplitude of about seventy-five percent (75%) of a peak value of a curve approximating the vascular pressure oscillations, wherein the first pressure value is higher than a pressure value corresponding to the peak value of the curve approximating the vascular pressure oscillations;
    generating an output that corresponds to the first pressure value; and
    identifying the output as a return of blood flow pressure at the vascular location.

5. The method of claim 4, wherein an orifice size of a variable orifice valve is changed over time for linearly decreasing the applied pressure at the vascular location.

6. The method of claim 4, wherein the vascular location is disposed at a human toe.

\* \* \* \* \*